United States Patent [19]

Edwards et al.

[11] Patent Number: 4,574,123
[45] Date of Patent: Mar. 4, 1986

[54] 4,4'-ALKYLENEDIPIPERIDINE DERIVATIVES

[75] Inventors: Philip N. Edwards, Bramhall; Michael S. Large, Congleton, both of England

[73] Assignee: Imperial Chemical Industries PLC, London, England

[21] Appl. No.: 606,688

[22] Filed: May 3, 1984

[30] Foreign Application Priority Data

May 9, 1983 [GB] United Kingdom ............... 8312665

[51] Int. Cl.$^4$ .................. C07D 401/14; A01N 43/40; A61K 31/445
[52] U.S. Cl. ............................. 514/210; 514/225; 514/212; 514/237; 514/316; 546/186; 546/187; 544/78; 544/127; 544/360
[58] Field of Search ............... 546/186, 187; 544/78, 544/127, 360; 514/255, 212, 210, 237, 316

[56] References Cited

U.S. PATENT DOCUMENTS 3,377,303  4/1968  Peerman ............... 564/186

FOREIGN PATENT DOCUMENTS 705838   3/1954   United Kingdom ............... 564/235
1095902  12/1967  United Kingdom ............... 564/235
1173244  12/1969  United Kingdom ............... 546/186
1438405  6/1979   United Kingdom ............... 544/293

*Primary Examiner*—Robert T. Bond
*Attorney, Agent, or Firm*—Cushman, Darby & Cushman

[57] ABSTRACT

A 4,4'-alkylenebis[piperidine-1-(N-amidinoamidine)] derivative of the formula:

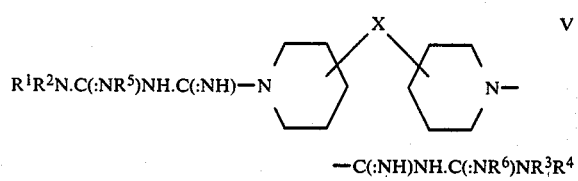

or a tautomeric form thereof, wherein each of $R^1$, $R^2$, $R^3$ and $R^4$, which may be the same or different, is hydrogen or an alkyl, alkenyl or alkoxyalkyl radical of up to 20 carbon atoms; or $R^1$, $R^2$ and the nitrogen atom to which they are attached, or $R^3$ and $R^4$ and the nitrogen atom to which they are attached, which may be the same or different, are each a 1-azetidinyl, 1-pyrrolidinyl, piperidino, hexamethyleneimino, heptamethyleneimino, morpholino or 4-(1-8C alkanoyl)-1-piperazinyl radical each of which may bear 1-3C alkyl substituents; a 3–20C cycloalkyl radical; or an optionally substituted phenyl or phenylalkyl radical; provided that at least one of $R^1$, $R^2$, $R^3$ and $R^4$ is other than hydrogen; X is a direct bond or a 1-6C straight- or branched-chain alkylene radical which is linked to the 3- or 4-positions of the piperidine rings; and $R^5$ and $R^6$, which may be the same or different, are each hydrogen or a 1-8C alkyl radical; and the acid addition salts thereof, processes for their manufacture, and antibacterial and antifungal compositions and methods using said compounds.

8 Claims, No Drawings

4,4'-ALKYLENEDIPIPERIDINE DERIVATIVES

This invention relates to novel 4,4'-alkylenedipiperidine derivatives, which possess antibacterial properties, and in particular to 4,4'-alkylenebis[piperidine-1-(N-amidinoamidine)] derivatives.

Certain bisbiguanide compounds are known to possess antibacterial properties. For example, in United Kingdom patent specification No. 705,838 there are disclosed and claimed bisbiguanides of the general formula:

A—NH.C(:NH)NH.C(:NH)NH—(CH$_2$-)$_n$—NH.C(:NH)NH.C(:NH)NH—A    I wherein A stands for a phenyl radical which is substituted by alkyl, alkoxy, nitro or halogen, and wherein the two A's may be the same or different, and wherein n is an integer from 3 to 9 inclusive, and wherein the polymethylene chain may be interrupted by oxygen atoms and/or by aromatic nuclei. The compounds are said to be useful as bactericides; for example, those of the formula:

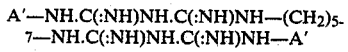

A'—NH.C(:NH)NH.C(:NH)NH—(CH$_2$)$_{5-7}$—NH.C(:NH)NH.C(:NH)NH—A'    II wherein A' stands for a halogen substituted phenyl radical possess very high antibacterial activity when tested in vitro against the organisms *Streptococcus haemolyticus, Staphylococcus aureus, Bacillus coli, Clostridium welchii* and *Pseudomonas pyrocyanea*.

In United Kingdom patent specification No. 1,095,902 there is disclosed and claimed a broad group of bisguanides and bisbiguanides which includes inter alia compounds of the formula:

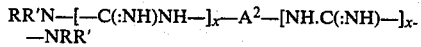

RR'N—[—C(:NH)NH—]$_x$—A$^2$—[NH.C(:NH)—]$_x$—NRR'    III wherein A$^2$ stands for an alkylene radical of 2 to 12 carbon atoms having the valency bonds attached to different carbon atoms, or for a group of the formula:

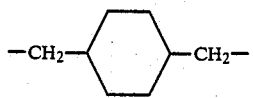

IV

R stands for an alkyl radical of 6 to 16 carbon atoms, R' stands for hydrogen, and x stands for 1 or 2. The bisguanides and bisbiguanides are said to have particular usefulness as plant fungicides and bactericides.

According to the present invention, there is provided a 4,4'-alkylenebis[piperidine-1-(N-amidinoamidine)] derivative of the formula:

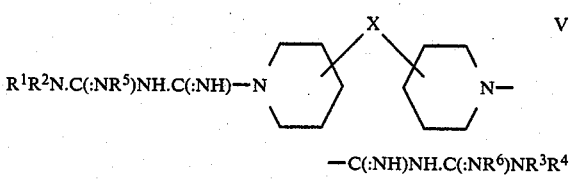

or a tautomeric form thereof, wherein each of R$^1$, R$^2$, R$^3$ and R$^4$, which may be the same or different, is hydrogen or an alkyl, alkenyl or alkoxyalkyl radical of up to 20 carbon atoms; or R$^1$, R$^2$ and the nitrogen atom to which they are attached, or R$^3$ and R$^4$ and the nitrogen atom to which they are attached, which may be the same or different, are each a 1-azetidinyl, 1-pyrrolidinyl, piperidino, hexamethyleneimino, heptamethyleneimino, morpholino or 4-(1-8C alkanoyl)-1-piperazinyl radical each of which may bear 1-3C alkyl substituents; a 3-20C cycloalkyl radical; or an optionally substituted phenyl or phenylalkyl radical; provided that at least one of R$^1$, R$^2$, R$^3$ and R$^4$ is other than hydrogen; X is a direct bond or a 1-6C straight- or branched-chain alkylene radical which is linked to the 3- or 4-positions of the piperidine rings; and R$^5$ and R$^6$, which may be the same or different, are each hydrogen or a 1-8C alkyl radical; and the acid addition salts thereof.

R$^1$, R$^2$, R$^3$, R$^4$, R$^5$ and R$^6$ when they are alkyl or alkenyl radicals, may be, for example, a methyl, ethyl, n-propyl, isopropyl, n-butyl, sec-butyl, isobutyl, n-pentyl, neopentyl, n-hexyl, 2-ethylhexyl, n-heptyl, n-octyl or allyl radical, and such radicals of 4 to 6 carbon atoms are preferred.

When they are alkoxyalkyl radicals, R$^1$, R$^2$, R$^3$ and R$^4$ may be, for example, 2-methoxyethyl, 2-ethoxyethyl, 2-n-butoxyethyl, 2-n-heptyloxyethyl, 3-n-butoxypropyl or 7-methoxyheptyl radicals.

When R$^1$ and R$^2$, and R$^3$ and R$^4$, together with the nitrogen atoms to which they are attached, form a heterocyclic radical, preferred such radicals are the 1-pyrrolidinyl and piperidino radicals, and a preferred alkyl-substituted such radical is, for example, the 2,6-dimethylmorpholino radical.

When one or more of R$^1$, R$^2$, R$^3$ and R$^4$ is an optionally substituted phenyl or phenylalkyl radical, it is preferably a phenyl, benzyl, α-methylbenzyl, α-ethylbenzyl or phenethyl radical, and suitable optional substituents in the phenyl ring thereof are, for example, halogen atoms, for example chlorine, bromine, iodine or fluorine atoms, amino, carbamoyl, cyano, hydroxy, nitro and trifluoromethyl radicals, 1-6C alkyl, alkoxy, alkanoyl, alkylamino and alkanoylamino radicals and 2-6C alkoxycarbonyl and dialkylamino radicals. Suitable such radicals are, for example, methyl, ethyl, propyl, butyl, pentyl, hexyl, methoxy, ethoxy, propoxy, acetamido, propionamido, butyramido, methylamino, ethylamino, propylamino, acetyl, propionyl, butyryl, methoxycarbonyl, ethoxycarbonyl, dimethylamino and diethylamino radicals. Up to five such substituents may be present, but mono- and di-substituted phenyl rings are preferred, and especially mono-substituted phenyl rings.

Thus, further suitable values for R$^1$, R$^2$, R$^3$ and R$^4$ are, for example, 2-, 3- and 4-chlorophenyl, 2-, 3- and 4-bromophenyl, 2-, 3- and 4-fluorophenyl, 2,3-, 2,4-, 2,5-, 2,6-, 3,4- and 3,5-dichlorophenyl, 2-chloro-4-fluorophenyl, 2-, 3- and 4-methylphenyl, 2,3-, 2,4-, 2,5-, 2,6- 3,4- and 3,5-dimethylphenyl, 2-, 3- and 4-methoxyphenyl, 2-, 3- and 4-acetylphenyl, 2-, 3- and 4-methylaminophenyl, 2-, 3- and 4-acetamidophenyl, 2-, 3- and 4-methoxycarbonylphenyl, 2-, 3- and 4-dimethylaminophenyl, 2-, 3- and 4-nitrophenyl, 2-, 3- and 4-chlorobenzyl, 2-, 3- and 4-bromobenzyl, 2-, 3- and 4-fluorobenzyl, 2,3-, 2,4-, 2,5-, 2,6-, 3,4- and 3,5-dichlorobenzyl, 2-chloro-4-fluorobenzyl, 2-, 3- and 4-methylbenzyl, 2,3-, 2,4-, 2,5-, 2,6-, 3,4- and 3,5-dimethylbenzyl, 2-, 3- and 4-methoxybenzyl, 2-, 3- and 4-acetylbenzyl, 2-, 3- and 4-methylaminobenzyl, 2-, 3- and 4-acetamidobenzyl, 2-, 3- and 4-methoxycarbonylbenzyl, 2-, 3- and 4-dimethylaminobenzyl, 2-, 3- and 4-nitrobenzyl, 2-, 3- and 4-chloro-α-methylbenzyl and 2-, 3- and 4-chlorophenethyl radicals.

A preferred phenylalkyl value for $R^1$, $R^2$, $R^3$ or $R^4$ is the phenethyl radical.

A preferred value for X is the trimethylene radical.

Particular preferred compounds of the invention are 4,4'-trimethylenebis[piperidine-1-(N,N-dibutylamidino)carboxamide], 4,4'-trimethylenebis[piperidine-1-(N-n-hexylamidino)-carboxamide], 4,4'-trimethylenebis[piperidine-1-(N-benzylamidino)carboxamide], 4,4'-trimethylenebis-[piperidine-1-(N-phenethylamidino)carboxamide] and 4,4'-trimethylenebis[piperidine-1-(N,N-di-isobutylamidino)carboxamide] and the dihydrochlorides thereof.

The acid-addition salts of the invention may be derived from an inorganic or organic acid. In most circumstances it is preferable that the salts be derived from an acid which affords an anion which is suitable for human usage, for example a pharmaceutically acceptable anion. Examples of such acids are hydrochloric, hydrobromic, phosphoric, sulphuric, acetic, D-gluconic, 2-pyrrolidone-5-carboxylic, methanesulphonic, carbonic, lactic and glutamic acids.

According to a further feature of the invention there is provided a process for the manufacture of the compounds of the invention wherein $R^5$ and $R^6$ are each hydrogen, which comprises reacting a bis-cyanoguanidine of the formula

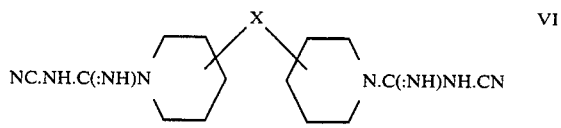

with an amine, $R^1R^2NH$ or with two different amines, $R^1R^2NH$ and $R^3R^4NH$ in the form of an acid-addition salt thereof, wherein X, $R^1$, $R^2$, $R^3$ and $R^4$ have the meanings stated above, at a temperature of 100° to 170° C.

A suitable amine salt is, for example, the hydrochloride. The reactants are heated together at, for example, 140° to 150° C. until the reaction is complete. The reaction proceeds fastest at higher temperature, but if thermal stability is a problem, the temperature should be lowered and the reaction allowed to proceed for longer. The reactants are most conveniently melted together in the absence of a solvent, but if desired an inert solvent such as 2-methoxyethanol, 2-ethoxyethanol, nitrobenzene, sulpholane, isopropanol, n-butanol, ethylene glycol dimethyl ether or water, or a mixture of such solvents may be used.

The bis-cyanoguanidines of the formula VI, which may be used as starting materials in the above process, may be obtained by reacting the appropriate bis-piperidine derivative of the formula:

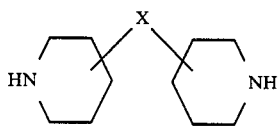

wherein X has the meaning stated above, in the form of an acid addition salt, conveniently the dihydrochloride, with sodium dicyanamide, $NaN(CN)_2$.

According to a further feature of the invention there is provided a process for the manufacture of the compounds of the invention which comprises reacting a diamine of the formula VII in the form of an acid-addition salt, with a cyanoguanidine of the formula:

or with a cyanoguanidine of the formula VIII and a cyanoguanidine of the formula:

and wherein X, $R^1$, $R^2$, $R^3$, $R^4$, $R^5$ and $R^6$ have the meanings stated above, at a temperature of 100° to 170° C.

A suitable salt of the diamine is, for example, the dihydrochloride. The reactants are heated together until the reaction is complete. The reaction proceeds fastest at higher temperature, but if thermal stability is a problem, the reaction should be carried out at lower temperature over a longer period. If a melt can be formed at those temperatures the reactants are conveniently melted together in the absence of a solvent. If not, or alternatively, the reactants are heated together in a suitable inert solvent, for example those mentioned above.

The cyanoguanidines of the formulae VIII and IX wherein $R^5$ and $R^6$ are hydrogen, which may be used as starting materials in the above process, may be obtained by reacting sodium dicyananide with an appropriate amine $R^1R^2NH$ or $R^3R^4NH$, in the form of an acid-addition salt, conveniently the dihydrochloride, in a suitable inert solvent.

The cyanoguanidines of the formulae VIII and IX wherein $R^5$ and $R^6$ are other than hydrogen, which may be used as starting materials in the above process, may be obtained by reacting a dialkyl(cyanoimido)dithiocarbonate, for example dimethyl(cyanoimido)dithiocarbonate, $(MeS)_2C:N.CN$, with appropriate amines $R^1R^2NH$ and $R^5NH_2$ (which are preferably the same), or $R^3R^4NH$ and $R^6NH_2$.

The acid-addition salts of the invention are obtained by conventional means.

The antibacterial activity of the compounds of the invention has been measured by the well-known minimum inhibitory concentration (MIC) test. Neat or diluted broth cultures of eight Gram positive organisms (*Streptococcus pyogenes*, *S. faecalis*, 3 strains of *Staphylococcus aureus*, *Listeria monocytogenes*, *Streptococcus mutans*, *S. sanguis*), *Candida albicans* and fourteen Gram negative organisms (4 strains of *Escherichia coli*, *Salmonella dublin*, *Klebsiella aerogenes*, *K. pneumoniae*, *E. cloacae*, *Serratia marcescens*, *Proteus vulgaris*, *P. mirabilis* and 3 strains of *Pseudomonas aeruginosa*) were inoculated by means of an automatic microtitre inoculator on the surface of nutrient agar plates containing two-fold or five-fold dilutions of a test compound. After incubation overnight at 37° C., the MIC's of the test compound are read. The geometric mean MIC's for the eight Gram positive organisms and Candida, and 14 Gram negative organisms are then calculated for each test compound.

Depending upon its precise chemical structure, a compound of the invention has a geometric mean minimum inhibitory concentration within the range 1-12 μg./ml. in agar against the 8 Gram positive organisms and Candida, and 20-250 μg./ml. in agar against the 14 Gram negative organisms.

The preferred compounds of the invention have an acute $LD_{50}$ within the accepted limits for compounds used topically, are of low irritancy in the Draize test on intact rabbit skin, are negative in the Ames test for mutagenicity, and are non-sensitizing in the Magnusson and Kligman contact sensitivity test in guinea-pigs.

Because of their antibacterial and antifungal properties, the compounds of the invention are useful for many purposes, for example (a) in medical and veterinary practice for the disinfection of wounds, membranes and/or skin tissue;

(b) for the sterilisation of surgical instruments and other medical apparatus and equipment, for example respirators, ventilators, incubators, humidifiers, etc.;

(c) for incorporation in toothpastes and mouthwashes for inhibiting the formation of dental plaque, and gingivitis;

(d) for the disinfection of hard surfaces, for example plant and equipment used in the food and drink industries, and floors and walls in the home, factories and hospitals;

(e) for the disinfection of textiles, for example blankets, overalls, bed-linen, etc.

(f) for the control of microbiological slime in the pulp and paper industries;

(g) for the control of micro-organisms in swimming pools, cooling water, pasteuriser water, aqueous oil emulsions such as metal working fluids, and other circulating water systems; and (h) and as plant bactericides and fungicides.

A drawback to the use of chlorhexidine is that if it contacts white textiles which are subsequently laundered with hypochlorite bleach, dark stains develop. It is an advantage of the preferred compounds of this invention that such staining is non-existent, or minimal.

Compounds of the invention also possess useful antifungal activity against, for example, *Candida albicans* and *Trichophyton mentagrophytes*, and algicidal and anti-yeast activity.

According to a further feature of the invention there are provided antibacterial or antifungal compositions comprising a compound of the formula V wherein $R^1$, $R^2$, $R^3$, $R^4$, $R^5$, $R^6$ and X have the meanings stated above, or an acid-addition salt thereof, and an inert diluent or carrier therefor.

The antibacterial or antifungal compositions of the invention are prepared by conventional means using conventional excipients. They include, for example, aqueous solutions, for example concentrated aqueous solutions, sterile, ready-to-use aqueous solutions, aqueous dispersions, and emulsions, for example oil-in-water emulsions, for example aqueous gels, creams, ointments and pastes. Suitable excipients include, for example, wetting agents, dispersing agents, emulsifying agents, gelling agents or thickening agents.

According to a further feature of the invention, there is provided a contraceptive method which comprises applying to sperm or the locus of sperm, a spermicidal, sperm-immobilising or mucospissic amount of a compound of the invention of the formula V.

In one aspect of this method, the compound of the formula V, when applied to vaginal mucus at a suitable concentration, very rapidly increases its viscosity, to the extent that it becomes essentially impenetrable to sperm, and forms a physical barrier to conception in the same way as a rubber sheath or a diaphragm cap.

Besides increasing the viscosity of vaginal mucus, when the mucus comes into contact with a bisbiguanide compound of the formula V, other changes occur in its intrinsic properties, such as its morphology, rheology and water uptake and visco-elastic properties, which can also effect its penetrability to sperm. The compounds also possess spermicidal or sperm-immbolising properties.

In vitro, the compounds of the formula V exert a useful contraceptive effect at concentrations down to about $10^{-3}$ to $10^{-4}\%$, and a suitable amount to be applied to the human vagina for contraceptive purposes is from 1.0 g. to $10^{-4}$ g.

The compound of the formula V may be applied to the vagina in conventional manner, for example as a pessary, cream, liquid douche, gel, aerosol foam or impregnated tampon, or in a controlled delivery device of the compound in a polymer matrix.

According to a further feature of the invention there is provided a compound of the formula V, or a composition thereof, for use as a contraceptive.

The invention is illustrated but not limited by the following Examples in which the temperatures are expressed in degrees Celsius:

EXAMPLES 1-15

An intimate mixture of 4,4'-trimethylenedi piperidine dihydrochloride (0.95 g.) and 3-cyano-1-isopropyl-guanidine (1.68 g.) was heated in a bath at 150° for 4 hours. The cooled mixture was dissolved in hot methanol (10 ml.), and the solution was filtered. The filtrate was diluted with acetone (200 ml.) and the solid that crystallised was collected, to give 4,4'-trimethylenebis[-piperidine-1-(isopropylamidino)carboxamidine]dihydrochloride m.p. 204°-206°.

The above process was repeated, using the appropriate bis-piperidine and cyanoguanidine starting materials, to give the following compounds:

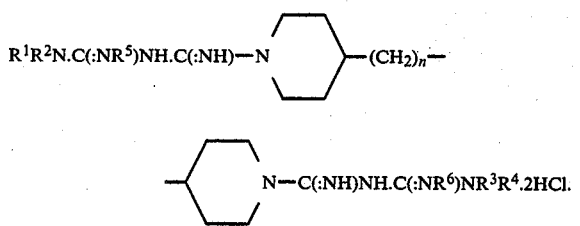

$R^1R^2N.C(:NR^5)NH.C(:NH)-N\bigcirc-(CH_2)_n-$ $-\bigcirc N-C(:NH)NH.C(:NR^6)NR^3R^4.2HCl.$

| No. | $R^1(=R^3)$ | $R^2(=R^4)$ | $R^5(=R^6)$ | n | Crystallisation solvent | Melting point |
|---|---|---|---|---|---|---|
| 2 | methyl | H | methyl | 3 | a | 185-188 |
| 3 | propyl | H | propyl | 3 | b | 84-88(d) |
| 4 | butyl | H | H | 3 | a | 183-186 |
| 5 | hexyl | H | H | 3 | c | 201-203(g,h) |
| 6 | cyclohexyl | H | H | 3 | a | 244-245(g,h) |
| 7 | benzyl | H | H | 3 | e | 263-264 |
| 8 | phenethyl | H | H | 3 | a | 199-202 |
| 9 | —(CH$_2$)$_5$— | | H | 3 | c | 202-204(g,h) |
| 10 | methyl | methyl | H | 0 | a | 246-248 |
| 11 | isopropyl | H | H | 0 | a | 251-252 |
| 12 | benzyl | H | H | 0 | a | 209-213 |
| 13 | phenethyl | H | H | 0 | a | 230-232 |
| 14 | hexyl | H | H | 0 | f | 212-214(g) |

-continued

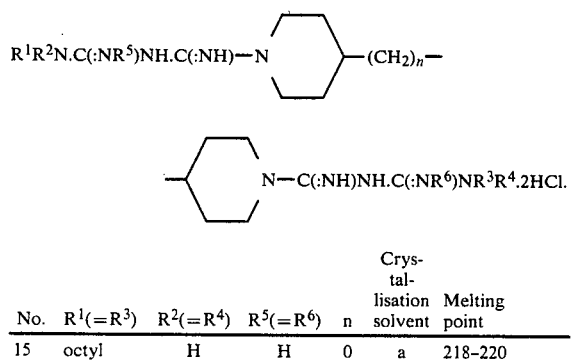

| No. | R¹(=R³) | R²(=R⁴) | R⁵(=R⁶) | n | Crystallisation solvent | Melting point |
|---|---|---|---|---|---|---|
| 15 | octyl | H | H | 0 | a | 218–220 | a — methanol/acetone
b — diethyl ether
c — acetone
d — with decomposition
e — methanol
f — ethanol
g — 1–2 ml. of sulpholane added to the reaction mixture before heating.
h — purified by medium pressure liquid chromatography on Merck "Lichoprep RP-18" (trade mark) eluting with an appropriate methanol/water mixture.

The 3-cyano-1-hexylguanidine used as starting material for Examples 5 and 15 may be obtained as follows:

A mixture of hexylamine hydrochloride (63.5 g.), sodium dicyanamide (44.5 g.) and butanol (200 ml.) was heated at reflux for 18 hours and then cooled. The mixture was filtered and the filtrate was evaporated to dryness. The residue was stirred with water and the isoluble solid was collected and crystallised from aqueous ethanol, to give 3-cyano-1-hexylguanidine, m.p. 103°–105°.

By a similar process using di-isobutylamine hydrochloride in place of n-hexylamine hydrochloride, there was thus obtained 1,1-di-isobutyl-3-cyanoguanidine m.p. 100°–101° (after crystallisation from a mixture of toluene and petroleum ether (boiling point 60°–80°).

The 3-cyano-1,2-dipropylguanidine used as the starting material in Example 2 was obtained as follows:

Propylamine (40 g.) was added to a solution of dimethyl(cyanoimido)dithiocarbonate, (MeS)₂C:N.CN, (20 g.) in ethanol (100 ml.) with stirring. Sufficient N,N-dimethylformamide was added to redissolve the white solid which precipitated, and the solution was kept at room temperature for 24 hours. The solution was evaporated to dryness and the residue was triturated with ethyl acetate to give 3-cyano-1,2-dipropylguanidine (16 g.) as an insoluble solid, which was filtered off and used without further purification.

Other 3-cyano-1-substituted-guanidines, 3-cyano-1,1-disubstituted-guanidines and 3-cyano-1,2-disubstituted-guanidines are obtained similarly, using the appropriate amine starting materials.

EXAMPLES 16–17

16. A mixture of 1,1-di-butyl-3-cyanoguanidine (18.9 g.), 4,4'-trimethylenebispiperidine dihydrochloride (6.82 g.) and butanol (10 ml.) was stirred at 120° C. (bath temperature) for 18 hours. The cooled mixture was boiled with acetone (300 ml.) and then cooled, and the insoluble white solid was filtered off and recrystallised first from a mixture of methanol and acetonitrile, and then from water, to give 4,4'-trimethylenbis-[piperidine-1-(N,N-dibutylamidino)carboxamidine]dihydrochloride, m.p. 206°–208°.

17. In a similar manner, using 1,1-di-isobutyl-3-cyanoguanidine in place of 1,1-di-butyl-3-cyanoguanidine, there was obtained 4,4'-trimethylenebis[piperidine-2-(N,N-di-isobutylamidino)carboxamidine]dihydrochloride, m.p. 230°–232°.

The cyanoguanidines used as starting materials in the preparation of the above compounds are prepared by the general processes described in the latter part of Examples 1–15.

EXAMPLE 18

A solution of 4,4'-trimethylenedipiperidine dihydrochloride (21.5 g.) and 3-cyano-1-isobutyl-1-propylguanidine (30.4 g.) in butanol (30 ml.) was heated under reflux in an oil bath for 6 hours and allowed to cool. Acetone was added (up to 6 fold dilution) and the insoluble product was separated by filtration, then dried.

The isolated solid was recrystallised twice from water to give 4,4'-trimethylenebis-[piperidine-(N-isobutyl-N'-propylamidino)carboxamidine]dihydrochloride, m.p. 205°–6°.

EXAMPLES 19–24

The process described in Example 18 was repeated, using the appropriate cyanoguanidine as starting material, to manufacture the following compounds. The crude product was not always precipitated from the reaction solution by acetone in which cases the products were isolated by diluting the crude butanol solutions with acetonitrile (6 fold), filtering off any insoluble residues, and precipitating the crude reaction product by the addition of an equal volume of acetone. The products were subsequently purified by recrystallisations from water, except Example 22, which was purified by medium pressure liquid chromatography on Merck Lichoprep RP-18, eluting with aqueous methanol.

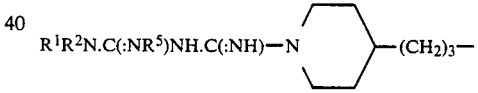

| No. | R¹(=R³) | R²(=R⁴) | R⁵(=R⁶) | M.p. |
|---|---|---|---|---|
| 19 | ethyl | ethyl | H | 214–215 |
| 20 | isopropyl | isopropyl | H | 190–191 |
| 21 | butyl | H | butyl | 100–102 |
| 22 | propyl | propyl | H | 198–200 |
| 23 | propyl | butyl | H | 194–195 |
| 24 | butyl | isobutyl | H | 219–221 (a) |

(a) — crystallised from acetonitrile/methanol.

The substituted cyanoguanidines used as starting materials in the preparation of the above compounds are prepared by the general processes described in the latter part of Examples 1–16 and were obtained crystalline by trituration with diethyl ether below 5°.

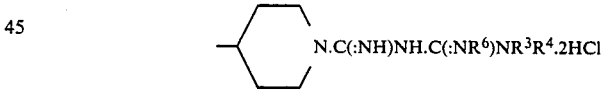

| R₁ | R₂ | M.p. |
|---|---|---|
| iPr | iBu | 77–80 |
| nPr | iBu | 79–81 |
| nPr | nBu | 52–53 |

-continued

| | $R^1R^2N-C(NH_2)=N.CN$ | |
|---|---|---|
| $R_1$ | $R_2$ | M.p. |
| nBu | iBu | (a) |

(a) — a gum, used without purification, but obtained from crystalline N—butyl-N—isobutylamine hydrochloride, m.p. 284–287⁻.

What we claim is:

1. A 4,4'-alkylenebis[piperidine-1-(N-amidinoamidine)] derivative of the formula:

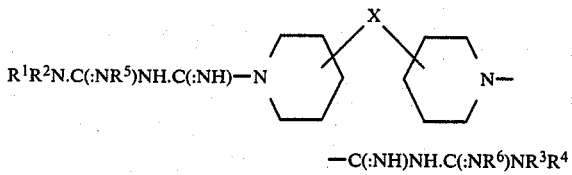

$$R^1R^2N.C(:NR^5)NH.C(:NH)-N$$

$$-C(:NH)NH.C(:NR^6)NR^3R^4$$

or a tautomeric form thereof, wherein each of $R^1$, $R^2$, $R^3$ and $R^4$, which may be the same or different, is hydrogen or an alkyl, alkenyl or alkoxyalkyl radical each having up to 20 carbon atoms; or $R^1$, $R^2$ and the nitrogen atom to which they are attached, or $R^3$ and $R^4$ and the nitrogen atom to which they are attached, which may be the same or different, are each a 1-azetidinyl, 1-pyrrolidinyl, piperidino, hexamethyleneimino, heptamethyleneimino, morpholino or 4-(1-8C alkanoyl)-1-piperazinyl radical each of which may bear 1–3C alkyl substituents; a 3–20C cycloalkyl radical; or a phenyl or phenylalkyl radical optionally substituted by chlorine, bromine, iodine or fluorine atoms, or by amino, carbamoyl, cyano, hydroxy, nitro, trifluoromethyl, methyl, ethyl, propyl, butyl, pentyl, hexyl, methoxy, ethoxy, propoxy, acetamido, propionamido, butyramido, methylamino, ethylamino, propylamino, acetyl, propionyl, butyryl, methoxycarbonyl, ethoxycarbonyl, dimethylamino or diethylamino radicals; provided that at least one of $R^1$, $R^2$, $R^3$ and $R^4$ is other than hydrogen; X is a direct bond or a 1–6C straight- or branched-chain alkylene radical which is linked to the 3- or 4-positions of the piperidine rings; and $R^5$ and $R^6$, which may be the same or different, are each hydrogen or a 1–8C alkyl radical; and the acid addition salts thereof.

2. A compound as claimed in claim 1 wherein each of $R^1$, $R^2$, $R^3$, $R^4$, $R^5$ and $R^6$ which may be the same or different, is hydrogen or a methyl, ethyl, n-propyl, isopropyl, n-butyl, sec-butyl, isobutyl, n-penyl, neopentyl, n-hexyl, 2- ethylhexyl, n-heptyl, n-octyl or allyl radical, or $R^1$, $R^2$, $R^3$ and $R^4$ which may be the same or different are each a 2-methoxyethyl, 2-ethoxyethyl, 2-n-butoxyethyl, 2-n-heptyloxyethyl, 3-n-butoxypropyl or 7-methoxyheptyl radical; or $R^1$ and $R^2$, or $R^3$ and $R^4$, together with the nitrogen atoms to which they are attached, which may be the same or different, are each a 1-pyrrolidinyl, piperidino or 2,6-dimethylmorpholino radical; or $R^1$, $R^2$, $R^3$ and $R^4$ which are the same or different, are each a phenyl, benyl, α-methylbenzyl, α-ethylbenzyl or phenethyl radical optionally substituted by chlorine, bromine, iodine or fluorine atoms, or by amino, carbamoyl, cyano, hydroxy, nitro, trifluoromethyl, methyl, ethyl, propyl, butyl, pentyl, hexyl, methoxy, ethoxy, propoxy, acetamido, propionamido, butyramido, methylamino, ethylamino, propylamino, acetyl, propionyl, butyryl, methoxycarbonyl, ethoxycarbonyl, dimethylamino or diethylamino radicals.

3. A compound as claimed in claim 2 wherein any of $R^1$, $R^2$, $R^3$ and $R^4$, which may be the same or different, is a phenyl, benzyl, α-methylbenzyl, α-ethylbenzyl, phenethyl, 2-, 3- or 4-chlorophenyl, 2-, 3- or 4-bromophenyl, 2-, 3- or 4-fluorophenyl, 2,3-, 2,4-, 2,5-, 2,6-, 3,4- or 3,5-dichlorophenyl, 2-chloro-4-fluorophenyl, 2-, 3- or 4-methylphenyl, 2,3-, 2,4-, 2,5-, 2,6-, 3,4- or 3,5-dimethylphenyl, 2-, 3- or 4-methoxyphenyl, 2-, 3- or 4-acetylphenyl, 2-, 3- or 4-methylaminophenyl, 2-, 3- or 4-acetamidophenyl, 2-, 3- or 4-methoxycarbonylphenyl, 2-, 3- or 4-dimethylaminophenyl, 2-, 3- or 4-nitrophenyl, 2-, 3- or 4-chlorobenzyl, 2-, 3- or 4-bromobenzyl, 2-, 3- or 4-fluorobenzyl, 2,3-, 2,4-, 2,5-, 2,6-, 3,4- or 3,5-dichlorobenzyl, 2-chloro-4-fluorobenzyl, 2-, 3- or 4-methylbenzyl, 2,3-, 2,4-, 2,5-, 2,6-, 3,4- or 3,5-dimethylbenzyl, 2-, 3- or 4-methoxybenzyl, 2-, 3- or 4-acetylbenzyl, 2-, 3- or 4-methylaminobenzyl, 2-, 3- or 4-acetamidobenzyl, 2-, 3- or 4-methoxycarbonylbenzyl, 2-, 3- or 4-dimethylaminobenzyl, 2-, 3- or 4-nitrobenzyl, 2-, 3- or 4-chloro-α-methylbenzyl or 2-, 3- or 4-chlorophenethyl radical, and X is a trimethylene radical.

4. A compound as claimed in claim 1 which is in the form of a salt with hydrochloric, hydrobromic, phosphoric, sulphuric, acetic, D-gluconic, 2-pyrrolidone-5-carboxylic, methanesulphonic, carbonic, lactic or glutamic acid.

5. A compound as claimed in claim 1 which is 4,4'-trimethylenebis[piperidine-1-(N,N-dibutylamidino)-carboxamidine], 4,4'-trimethylenebis[piperidine-1-(N-n-hexylamidino)-carboxamidine], 4,4'-trimethylenebis[piperidine-1-(N-benzylamidino)carboxamidine], 4,4'-trimethylenebis-[piperidine-1-(N-phenethylamidino)-carboxamidine] or 4,4'-trimethylenebis[piperidine-1-(N,N-di-isobutylamidino)carboxyamidine] or a dihydrochloride thereof.

6. An antibacterial or antifungal composition comprising an effective antibacterial or antifungal amount of a compound as claimed in claim 1 and an inert diluent or carrier therefor.

7. A method of obtaining an antibacterial or antifungal effect:
  (a) in medical and veterinary practice for the disinfection of wounds, membranes or skin tissue;
  (b) in the sterilisation of surgical instruments and other medical apparatus and equipment;
  (c) in toothpastes and mouthwashes for inhibiting gingivitis and the formation of dental plaque;
  (d) in the disinfection of hard surfaces;
  (e) in the disinfection of textiles;
  (f) in the control of microbiological slime in the pulp and paper industries;
  (g) in the control of micro-organisms in the swimming pools, cooling water, pasteuriser water, aqueous oil emulsions and other circulating water systems; or
  (h) against plant bacteria and/or fungi;
which comprises applying an antibacterially- or antifungally-effective amount of a bisbiguanide as claimed in claim 1 to the bacterially or fungally affected locus.

8. A contraceptive method which comprises applying to sperm, or the locus of sperm, a spermicidal, sperm-immobilising or mucospissic amount of a compound as claimed in claim 1.

* * * * *